United States Patent
Caby et al.

(10) Patent No.: US 8,890,702 B2
(45) Date of Patent: Nov. 18, 2014

(54) DEFIBRILLATOR DELIVERING AUDIBLE PROMPTS TO EARPIECE

(75) Inventors: Glen Caby, Kirkland, WA (US);
Richard C. Nova, Kirkland, WA (US);
John Daynes, Redmond, WA (US);
Ryan F. Landon, Redmond, WA (US)

(73) Assignee: Physio-Control, Inc., Redmond, WA (US)

( * ) Notice: Subject to any disclaimer, the term of this patent is extended or adjusted under 35 U.S.C. 154(b) by 204 days.

(21) Appl. No.: 13/016,871

(22) Filed: Jan. 28, 2011

(65) Prior Publication Data

US 2012/0105238 A1    May 3, 2012

Related U.S. Application Data

(60) Provisional application No. 61/409,053, filed on Nov. 1, 2010.

(51) Int. Cl.
*A61N 1/39* (2006.01)
*G08B 21/00* (2006.01)

(52) U.S. Cl.
CPC .............. *A61N 1/3993* (2013.01); *A61N 1/3925* (2013.01); *A61N 1/39* (2013.01)
USPC .............. 340/635; 340/539.12; 607/4; 607/5; 607/60

(58) Field of Classification Search
USPC .............. 340/531, 539.1–539.13, 573.1, 635, 340/679; 128/903, 904; 601/23; 607/2–15, 607/27, 30, 32, 60
See application file for complete search history.

(56) References Cited

U.S. PATENT DOCUMENTS

| | | | | |
|---|---|---|---|---|
| 5,593,426 A | * | 1/1997 | Morgan et al. | 607/5 |
| 5,790,897 A | * | 8/1998 | Corder et al. | 710/72 |
| 5,815,126 A | * | 9/1998 | Fan et al. | 345/8 |
| 6,334,070 B1 | | 12/2001 | Nova et al. | |
| 6,438,417 B1 | * | 8/2002 | Rockwell et al. | 607/5 |
| 6,597,949 B1 | * | 7/2003 | Dhurjaty | 607/5 |
| 6,611,708 B1 | * | 8/2003 | Morgan et al. | 607/5 |
| 7,120,488 B2 | * | 10/2006 | Nova et al. | 607/2 |
| 8,078,288 B2 | * | 12/2011 | Heath | 607/142 |
| 2003/0195567 A1 | | 10/2003 | Jayne | |
| 2003/0212311 A1 | | 11/2003 | Nova | |

(Continued)

FOREIGN PATENT DOCUMENTS

| | | |
|---|---|---|
| DE | 202008016123 U1 | 2/2009 |
| NL | WO2005/082454 A1 | 9/2005 |
| NL | WO 2006/016288 A1 | 2/2006 |
| WO | WO 03103765 A | 12/2003 |

OTHER PUBLICATIONS

International Search Report and Written Opinion, Apr. 26, 2012, 16 pages.

(Continued)

*Primary Examiner* — Benjamin C Lee
*Assistant Examiner* — Stephen Burgdorf
(74) *Attorney, Agent, or Firm* — Marger Johnson & McCollom PC

(57) ABSTRACT

Defibrillators, software and methods are provided, for transmitting inaudible audio information to one or more external personal sound devices. The audio information may encode an audible indication, which can thus be played by an external personal sound device to a user such as a rescuer.

20 Claims, 8 Drawing Sheets

(56) References Cited

U.S. PATENT DOCUMENTS

| | | |
|---|---|---|
| 2004/0015191 A1 | 1/2004 | Otman et al. |
| 2004/0027245 A1 | 2/2004 | Schlanger |
| 2006/0073787 A1* | 4/2006 | Lair et al. .................... 455/41.1 |
| 2006/0197656 A1* | 9/2006 | Sergio et al. ............. 340/539.11 |
| 2008/0077185 A1* | 3/2008 | Pearce et al. ....................... 607/5 |
| 2010/0054519 A1* | 3/2010 | Mulvey et al. ................ 381/386 |
| 2010/0114218 A1 | 5/2010 | Heath |
| 2011/0284004 A1* | 11/2011 | Silver et al. .............. 128/205.13 |
| 2011/0287719 A1* | 11/2011 | Pinder et al. ................. 455/41.3 |
| 2014/0155787 A1* | 6/2014 | Freeman et al. .............. 600/595 |

OTHER PUBLICATIONS

International Search Report and Written Opinion, Patent Cooperation Treaty, Apr. 26, 2012, 11 pages, PCT/US2011/058658, European Patent Office.

* cited by examiner

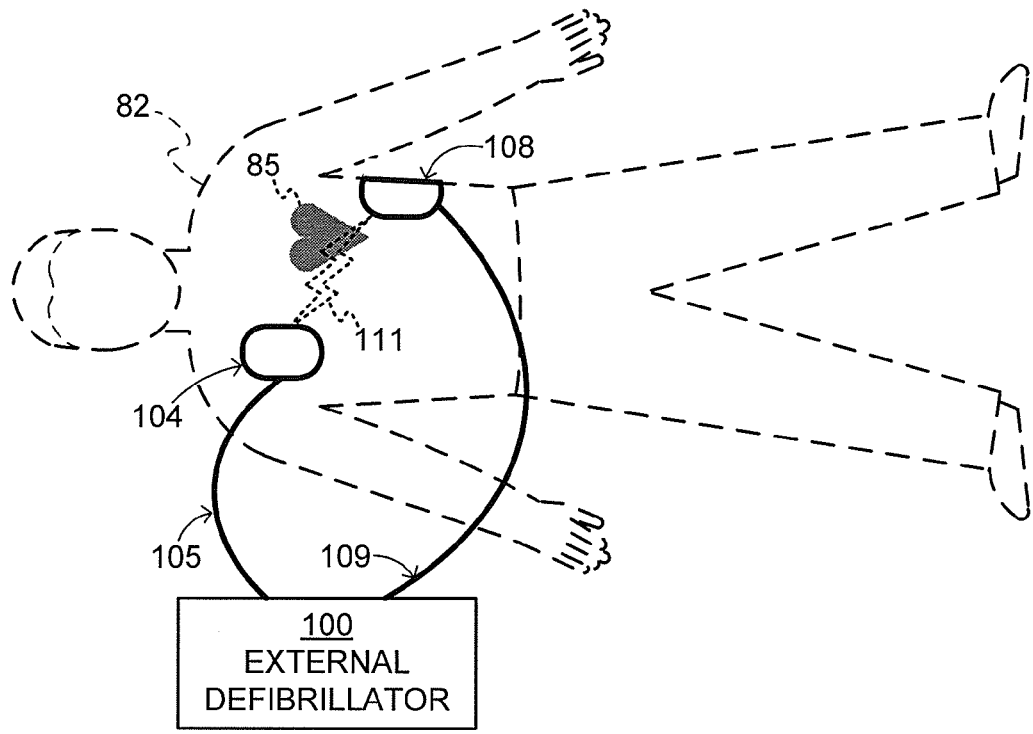
FIG. 1  *DEFIBRILLATION SCENE*
| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |
FIG. 2  *TWO MAIN TYPES OF EXTERNAL DEFIBRILLATORS*

COMPONENTS OF DEFIBRILLATOR

METHODS

METHODS

METHODS

DEFIBRILLATOR DELIVERING AUDIBLE PROMPTS TO EARPIECE

RELATIONSHIP WITH OTHER APPLICATIONS

This patent application claims priority from U.S. Provisional Patent Application Ser. No. 61/409,053, filed on Nov. 1, 2010, the disclosure of which is hereby incorporated by reference for all purposes.

This patent application may be found to be related to U.S. patent application Ser. No. 13/016,882, titled DEFIBRILLATOR WITH MUTABLE SOUND PROMPTS, assigned to the same assignee and filed on the same day as the instant patent application.

FIELD

This invention generally relates to the field of defibrillators and resuscitation.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body.

The heart chambers pump because of the heart's electrical control system. More particularly, the sinoatrial (SA) node generates an electrical impulse, which generates further electrical signals. These further signals cause the above-described contractions of the various chambers in the heart, in the right sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia, and some of it may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood. The person's condition will deteriorate rapidly and, if not reversed in time, they will die soon, e.g. within ten minutes.

Ventricular Fibrillation can often be reversed using a lifesaving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them.

During VF, the person's condition deteriorates, because the blood is not flowing to the brain, heart, lungs, and other organs. Blood flow must be restored, if resuscitation attempts are to be successful.

Cardiopulmonary Resuscitation (CPR) is one method of forcing blood flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows the deterioration that would otherwise occur while a defibrillator is being retrieved. Indeed, for patients with an extended down-time, survival rates are higher if CPR is administered prior to defibrillation.

It is desired to improve patient outcomes, by making improved decisions of when to administer therapy, such as electrical shocks, CPR, pharmaceuticals, etc. Patient outcomes are sometimes analyzed in post-event review.

BRIEF SUMMARY

The present description gives instances of medical devices, software and methods, the use of which may help overcome problems and limitations of the prior art.

In some embodiments, a defibrillator includes an audible indication control module that interacts with a processor and a communication module. Individual channels may be established between the communication module and each of one or more external personal sound devices.

Embodiments include a defibrillator configured to determine that an audible indication, such as a verbal prompt is to be delivered to a user and, responsive to such determination, transmit to an external personal sound device inaudible audio information corresponding to the audible indication. The external personal sound device may then transmit the audible indication to the user.

An advantage over the prior art is by the fact that a defibrillator may provide some or all of its audible indications discreetly, without have them be heard by the bystanders. As such, bystanders who may be loved ones of the person being cared for might not become additionally stressed by some of the normal audible indications.

Another advantage is that the audible indications may be delivered to a rescuer's earpiece. As such, they may be heard above and beyond ambient noise. Plus, additional ambient sounds have less of a chance of being misinterpreted as prompts.

One more advantage is that different sound indications may be transmitted concurrently to rescuers of different qualifications and training. Or speakers of different languages.

A further advantage is that sound indications can be delivered to rescuers who are remote to the scene, such as those arriving in an ambulance, or waiting for the patient at a treatment center.

These and other features and advantages of this description will become more readily apparent from the following Detailed Description, which proceeds with reference to the drawings, in which:

BRIEF DESCRIPTION OF THE DRAWINGS

FIG. 1 is a diagram of a scene where an external defibrillator is used to save the life of a person according to embodiments.

FIG. 2 is a table listing two main types of the external defibrillator shown in FIG. 1, and who they might be used by.

DETAILED DESCRIPTION

Figure 3:
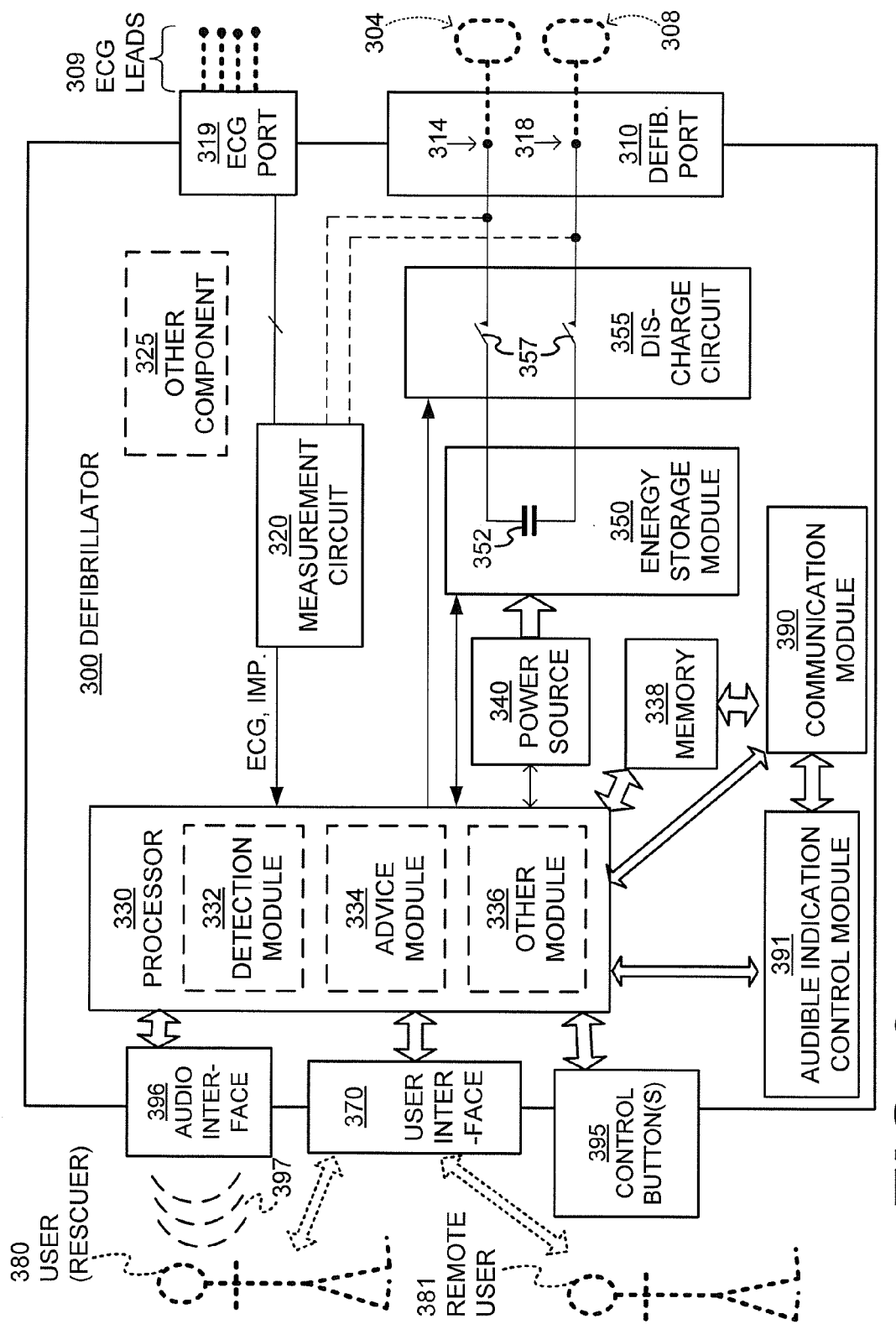
FIG. 3 is a diagram showing components of a defibrillator, such as the one shown in FIG. 1, which is made according to embodiments.

As has been mentioned, the present description is about making a decision of whether electric therapy should be administered or not. Embodiments include medical devices that can administer electrical therapy, such as defibrillators, pacers, etc. Examples are now described.

FIG. 1 is a diagram of a defibrillation scene. A person 82 is lying on their back. Person 82 could be a patient in a hospital, or someone found unconscious, and then turned to be on their back. Person 82 is experiencing a condition in their heart 85, which could be Ventricular Fibrillation (VF).

A portable external defibrillator 100 has been brought close to person 82. At least two defibrillation electrodes 104, 108 are usually provided with external defibrillator 100, and are sometimes called electrodes 104, 108. Electrodes 104, 108 are coupled with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, goes also through heart 85, in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

FIG. 2 is a table listing two main types of external defibrillators, and who they are primarily intended to be used by. A first type of defibrillator 100 is generally called a defibrillator-monitor, because it is typically formed as a unit with a patient monitor. A defibrillator-monitor is intended to be used by persons in the medical professions, such as doctors, nurses, paramedics, emergency medical technicians, etc. Such a defibrillator-monitor is intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological signals of a person in an emergency scenario. For example, these signals can include a person's full ECG (electrocardiogram) signals. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is at an Intensive Care Unit, and so on.

AEDs, however, can also be used by people who are not in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Indeed, the people who will first reach the VF sufferer may not be in the medical professions.

Increasing awareness has resulted in AEDs being deployed in public or semi-public spaces, so that even a member of the public can use one, if they have obtained first aid and CPR/AED training on their own initiative. This way, defibrillation can be administered soon enough after the onset of VF, to hopefully be effective in rescuing the person.

There are additional types of external defibrillators, which are not listed in FIG. 2. For example, a hybrid defibrillator can have aspects of an AED, and also of a defibrillator-monitor. A usual such aspect is additional ECG monitoring capability.

FIG. 3 is a diagram showing components of an external defibrillator 300 made according to embodiments. These components can be, for example, in external defibrillator 100 of FIG. 1.

External defibrillator 300 is intended for use by a user 380, who would be the rescuer. According to embodiments, the external defibrillator may also be used by a remote user 381 such as a physician who is currently out of town but able to communicate with the defibrillator 300 over a wired or wireless connection, for example.

Defibrillator 300 typically includes a defibrillation port 310, such as a socket. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding via electrodes to person 82 an electrical charge that has been stored in defibrillator 300, as will be seen later in this document.

If defibrillator 300 is actually a defibrillator-monitor, as was described with reference to FIG. 2, then it will typically also have an ECG port 319, for plugging in ECG leads 309. ECG leads 309 can sense a full ECG signal. Moreover, a defibrillator-monitor could have additional ports (not shown), and an other component 325 for additional features.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions. In addition, if other component 325 is provided, it may be operated in part by processor 330, etc.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for user 380, etc.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes one or more capacitors 352, and so on.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

Defibrillator 300 further includes a user interface 370 for user 380 or remote user 381. User interface 370 can be made in any number of ways. For example, interface 370 may include a screen, to display what is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

One or more control buttons 395 can be used to enable the user 380 to provide certain commands to the defibrillator 300 as input. Responsive to the user 380 or an other user interacting with one or more of the control button(s) 395, the processor 330 can execute instructions to control the module or component to be affected based on the input. For example, the control button(s) 395 can be used to direct the processor 330 to instruct the communication module 390 to provide certain information to one or more external devices over a wired or wireless connection.

An additional feature of a defibrillator can be CPR-prompting. Prompts are issued to the user, visual or by sound, so that the user can administer CPR. Examples are taught in U.S. Pat. Nos. 6,334,070 and 6,356,785. In certain embodiments, such prompts can be issued to the user 380 as sound waves 397 emanating from an audio interface 396 such as a speaker, for example.

The defibrillator 300 can further include an audible indication control module 391 that can interact with the processor 330 and communication module 390. In certain embodiments, the audible indication control module 391 is a module in processor 330. The audible indication control module 391 can determine whether an audible indication such as a prompt, for example, is to be issued to the user 380.

The communication module 390 can be configured to, responsive to the processor 330 or audible indication control module 391 determining that an audible indication is to be issued, transmit inaudible audio information corresponding to the audible indication to at least one external personal sound device, the transmitted audio information being inaudible to the user.

Figure 4:
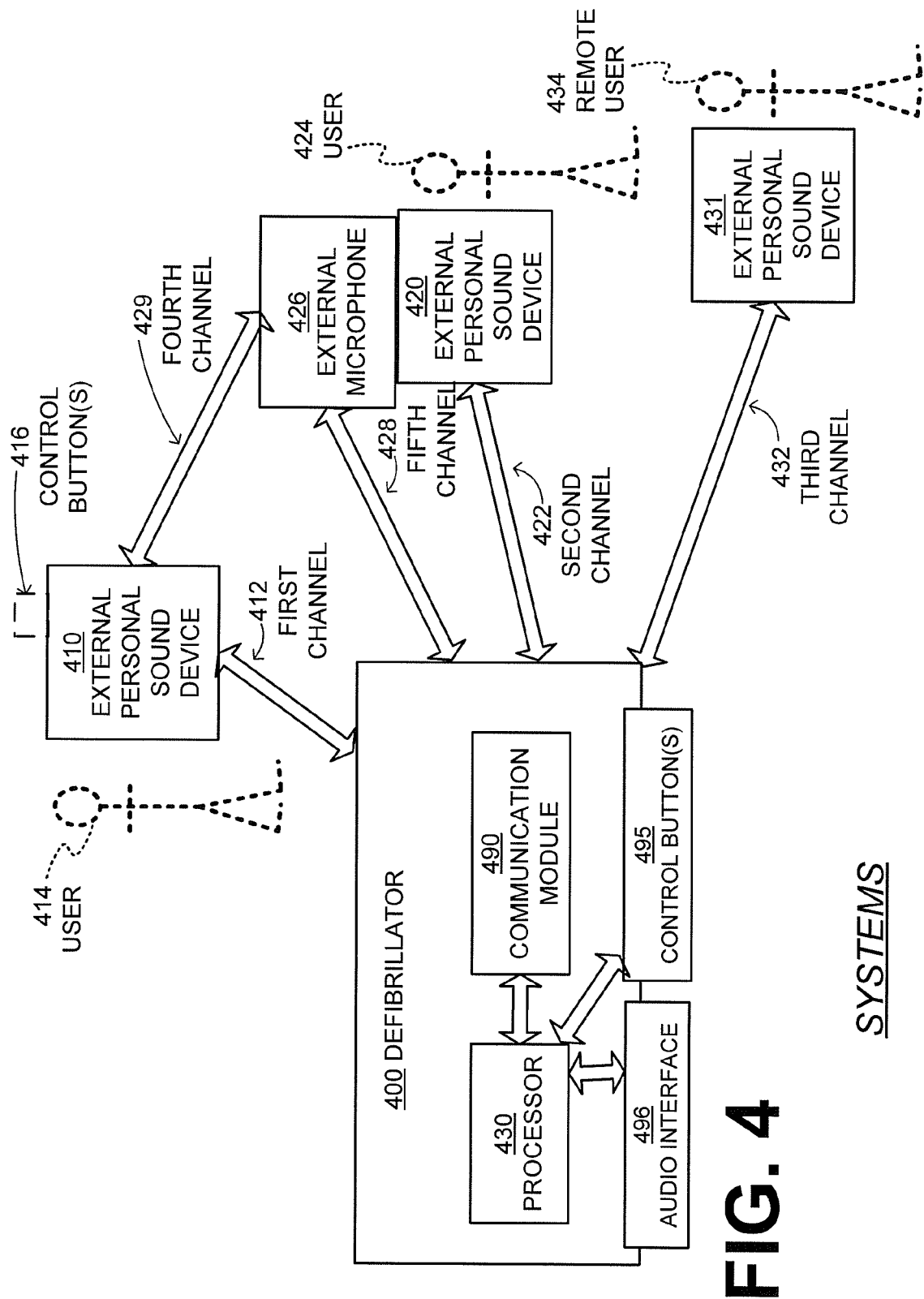
FIG. 4 is a diagram showing a defibrillator interacting with external devices, such as external personal sound devices, according to embodiments.

FIG. 4 is a diagram showing a defibrillator 400, such as the defibrillator 300 of FIG. 3, for caring for a person. Defibrillator 400 can be used with at least one external personal sound device that is configured to receive inaudible audio information, such as a signal. The audio information is inaudible in that it cannot be heard by the rescuers, but may correspond to an audible indication—for example the intended audible indication may be encoded in the audio information. Responsive to receiving the audio information, defibrillator 400 may deliver the audible indication to a user who is caring for the person. The audible indication can comprise one of an alert pertaining to the defibrillator 400, a prompt directing a rescuer to perform a particular action with respect to the patient receiving care, or the like. For example, the audible indication can be a characteristic sound indicating that a capacitor of the defibrillator is gradually being charged for delivering a shock—the capacitor itself makes no such sound but such a sound is created for the benefit of the rescuer. In certain embodiments, the external personal sound device may be configured to filter ambient noise from the audible indication delivered to the user using any of a number of suitable filtering techniques.

Defibrillator 400 includes a processor 430, such as the processor 330 of FIG. 3, which can provide instructions to and optionally receive information from a communication module 490. Communication module 490 may be made, for example such as was described in connection with communication module 390 of FIG. 3. Defibrillator 400 may also include one or more control buttons 495 that can be used to enable a user to provide input, such as instructions, to the processor 430. For example, the first user 414 may adjust the volume of audible indications delivered by the first external personal sound device 410 by way of the control button(s) 495.

Defibrillator 400 may include an audio interface 496, such as a speaker, for optionally delivering the audible indication to the user. In certain embodiments, the processor 430 is configured to monitor for connections, i.e., channels, to the communication module 490. Responsive to at least one external personal sound device establishing a connection with the communication module 490, the processor 430 may cause the audible indication to not be delivered via the speaker, effectively muting the speaker.

A first channel 412 may be established between the defibrillator 400 and a first external personal sound device 410 used by a first user 414. A second channel 422 may be established between the defibrillator 400 and a second external personal sound device 420 used by a second user 424. A third channel 432 may be established between the defibrillator 400 and a third external personal sound device 431 used by a remote user 434.

One or both of the sound devices 410 and 420 may be configured to deliver a connection signal, which would indicate that these devices are maintaining a connection to the communication module 490. The connection signal may be one of an audible signal, a visual signal, and a tactile signal. In some embodiments, the connection signal is delivered via a user interface of the defibrillator, such as interface 370. In some embodiments, the connection signal is delivered to one or both of the sound devices 410, 420 as supplementary audio information. In some embodiments, connection signals are delivered both via the user interface and the sound devices.

One or both of users 414 and 424 may be a rescuer, who could be located close to the person, for example no more than 10 feet (approximately 3 meters) away from the person. Alternatively or in addition thereto, one or both of users 414 and 424 may be remote, and in remote communication with the defibrillation scene of FIG. 1. In such instances, such a user can be located at least 300 feet (approximately 91 meters) away from the person, in fact much farther than that, such arriving via ambulance, or even waiting for the person at a treatment center.

In embodiments where the third sound device 431 is located remotely from the defibrillator 400, and the third channel 432 includes a wireless connection, the sound device 431 can be configured to receive inaudible audio information from the communication module 490 through the wireless connection. In certain embodiments, the wireless connection is a telephone connection to a telephone number, such as the telephone number of a remote rescuer.

One or more of the external personal sound devices 410, 420, 431 may comprise an earpiece. In certain embodiments, the earpiece can be configured to be coupled with a helmet configured to be worn by the user. Alternatively or in addition thereto, the earpiece can be configured to be coupled with a wearable display unit. Moreover, measures can be taken to ensure the cleanliness of the earpieces, especially considering that, at least for an AED, the user could be a passerby. Such measures can include sleeves over the earpieces, similar to those of digital thermometers. Or storage units that disinfect the earpieces using a method such as UV or some form of liquid or gas cleaner. Such measures preferably do not confuse a user as to what to do, while concurrently conveying to the user the confidence that the earpiece is clean.

The sound device 410 can optionally have one or more control buttons 416, or other interface implements, for enabling a user to control certain features of the sound device 410, as described below.

In some embodiments, at least one external microphone 426 is used to capture a voice from the second user 424. In these embodiments, the communication module is further configured to transmit the captured voice as additional audio information to at least one of the other external sound devices 410 and 431, for example by suitable operation of the processor. The communication module may be configured to transmit the additional audio information to only one of the other sound devices 410 and 431. For example, a fourth channel may be established between the communication module and the first sound device 410. For example, a fifth channel may be established between the external microphone 426 and the defibrillator 400.

The at least one external microphone 426 may be coupled with the second sound device 420. For example, the second sound device 420 may be configured to be attached to a helmet to which the external microphone 426 may also be attached.

Figure 5:
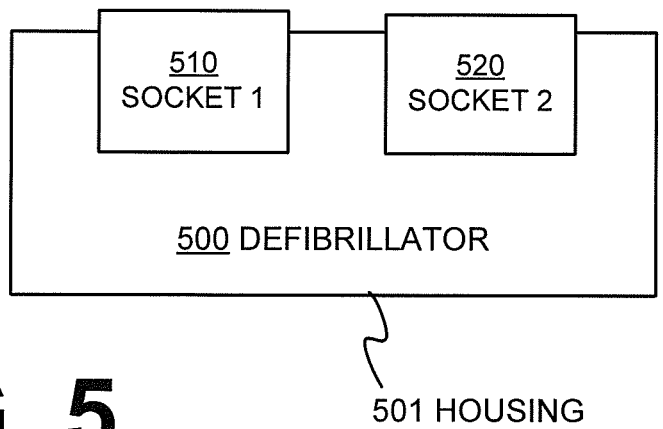
FIG. 5 is a diagram showing a defibrillator having two sockets according to embodiments.

FIG. 5 is a diagram showing a defibrillator 500, such as the defibrillator 300 of FIG. 3 or defibrillator 400 of FIG. 4, having multiple sockets 510 and 520 in the defibrillator housing 501 according to embodiments. In certain embodiments, at least one sound device is configured to receive inaudible audio information from a communication module, such as the communication module 490 of FIG. 4, through a wired connection. The sockets 510 and 520 may be virtually any type of socket suitable to be used with a defibrillator, such as audio-type or USB-type.

A sound device may include a plug configured to be received matingly in one of the sockets 510 and 520. The communication module can be configured to transmit different inaudible audio information by way of the first socket 510 and the second socket 520. The first socket 510 may be configured to provide a first output, e.g. for ALS-type rescuers, while the second socket 520 may be configured to provide a second output, e.g., for BLS-type rescuers. The defibrillator 500 may also include a housing that includes an energy storage module, such as the energy storage module 350 of FIG. 3. As per the above, the sockets can be on the housing. Each of the sockets 510 and 520 may have a label on the housing indicating the type of output provided by the socket.

In certain embodiments, both sockets 510 and 520 may be configured to provide the same output. In other embodiments, the first output of socket 510 may be different from the second output of socket 520. In some embodiments, multiple sockets may be provided for the same type of output, etc.

Socket outputs can be different in a number of ways. In some embodiments, different sockets can be for different languages. For example, in the USA, it may be advantageous to provide sockets for both English and Spanish. Moreover, if a speaker of the defibrillator has not been selectively muted, as is described elsewhere in this document, some rescuers can hear the speaker in one language, while another may establish a connection to listen in another.

Socket outputs can further be different as to which type of rescuer they are intended for, depending on the level of training. An example is described below.

Figure 6:
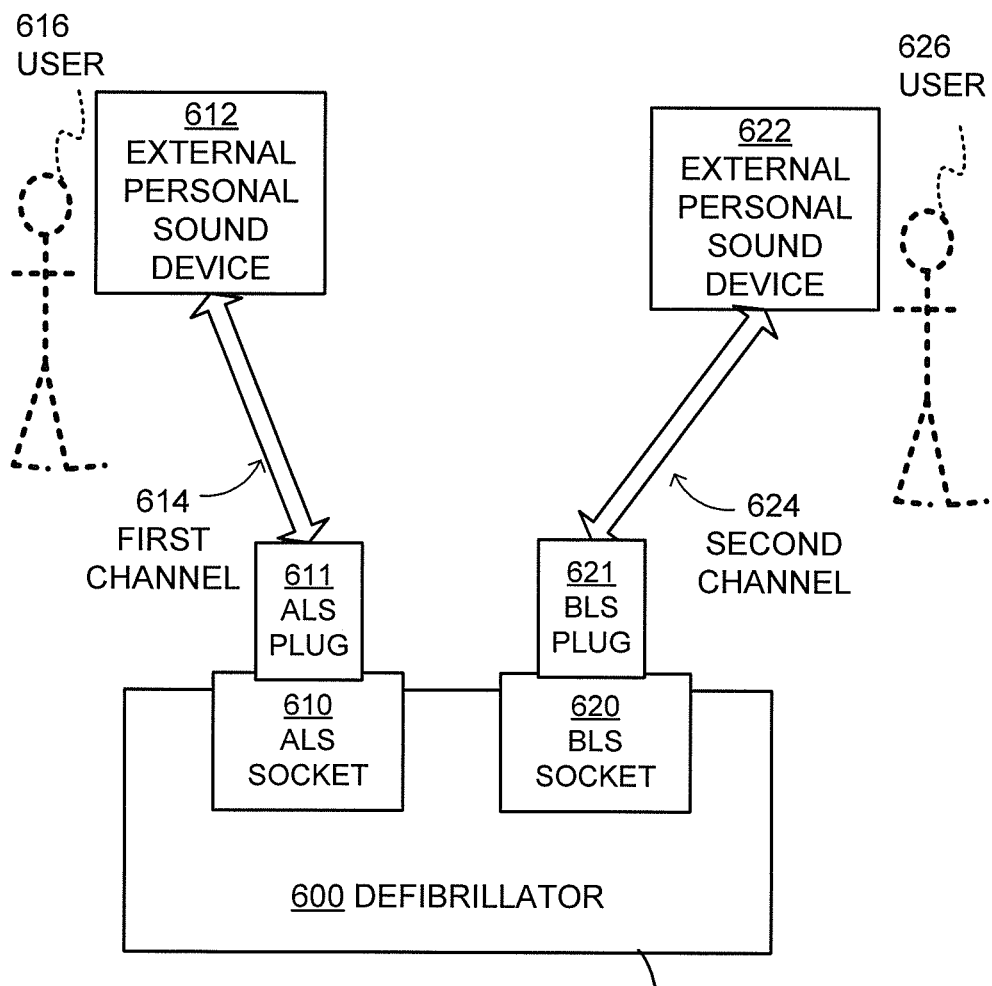
FIG. 6 is a diagram showing a defibrillator interacting with external devices, such as external personal sound devices, by way of sockets.

FIG. 6 is a diagram showing a defibrillator 600, such as the defibrillator 500 of FIG. 5, interacting with external devices, such as external personal sound devices, by way of an ALS socket 610 and a BLS socket 620 in the defibrillator housing 601. The ALS socket would be intended for Advanced Life Support personnel, while the BLS socket would be intended for Basic Life Support ("BLS") personnel.

A communication module, such as the communication module 490 of FIG. 4, may be configured to transmit inaudible audio information corresponding to an audible indication to a plurality of external personal sound devices 612 and 622 that are being used by two users 616 and 626, respectively. In certain embodiments, different inaudible audio information can be transmitted to the two sound devices 612 and 622.

A first channel 614 may be established between the ALS socket 610 and a first sound device 612 by way of an ALS plug 611 that can be matingly received by the ALS socket 610. A second channel 624 may be established between the BLS socket 620 and a second sound device 622 by way of a BLS plug 621 that can be matingly received by the BLS socket 620. At least one of the sound devices 612 and 622 may be located remotely from the defibrillator 600. This way, BLS personnel would plug their sound devices into one socket, while ALS personnel would plug their sound devices into the other socket.

The defibrillator 600 may further include a memory, such as the memory 338 of FIG. 3, for storing prompt data that correspond to prompts in at least two different human languages. Prompt data that corresponds to one of the languages may be transmitted as the inaudible audio information to one of the sound devices 612 and 622 according to a received language selection input. The language input selection may be provided by way of a control button, such as the control button(s) 395 of FIG. 3, on the defibrillator 600. The sound device may then transmit the corresponding audible indication to the user in the selected language.

Prompt data that corresponds to the other one of the languages may be transmitted as the inaudible audio information to the other one of the sound devices 612 and 622 according to an other received language selection input. The other language selection input may be provided by way of the same control button or by way of a different control button. The other one of the sound devices may then transmit the corresponding audible indication to the other user in the other language.

The functions of this description may be implemented by one or more devices that include logic circuitry. The device performs functions and/or methods as are described in this document. The logic circuitry may include a processor that may be programmable for a general purpose, or dedicated, such as microcontroller, a microprocessor, a Digital Signal Processor (DSP), etc. For example, the device may be a digital computer like device, such as a general-purpose computer selectively activated or reconfigured by a computer program stored in the computer. Alternately, the device may be implemented by an Application Specific Integrated Circuit (ASIC), etc.

Moreover, methods are described below. The methods and algorithms presented herein are not necessarily inherently associated with any particular computer or other apparatus. Rather, various general-purpose machines may be used with programs in accordance with the teachings herein, or it may prove more convenient to construct more specialized apparatus to perform the required method steps. The required structure for a variety of these machines will become apparent from this description.

In all cases there should be borne in mind the distinction between methods in this description, and the method of operating a computing machine. This description relates both to methods in general, and also to steps for operating a computer and for processing electrical or other physical signals to generate other desired physical signals.

Programs are additionally included in this description, as are methods of operation of the programs. A program is generally defined as a group of steps leading to a desired result, due to their nature and their sequence. A program is usually advantageously implemented as a program for a computing machine, such as a general-purpose computer, a special purpose computer, a microprocessor, etc.

Storage media are additionally included in this description. Such media, individually or in combination with others, have stored thereon instructions of a program made according to the invention. A storage medium according to the invention is a computer-readable medium, such as a memory, and is read by the computing machine mentioned above.

Performing the steps or instructions of a program requires physical manipulations of physical quantities. Usually, though not necessarily, these quantities may be transferred, combined, compared, and otherwise manipulated or processed according to the instructions, and they may also be stored in a computer-readable medium. These quantities include, for example electrical, magnetic, and electromagnetic signals, and also states of matter that can be queried by such signals. It is convenient at times, principally for reasons of common usage, to refer to these quantities as bits, data bits, samples, values, symbols, characters, images, terms, numbers, or the like. It should be borne in mind, however, that all of these and similar terms are associated with the appropriate physical quantities, and that these terms are merely convenient labels applied to these physical quantities, individually or in groups.

This detailed description is presented largely in terms of flowcharts, display images, algorithms, and symbolic representations of operations of data bits within at least one computer readable medium, such as a memory. Indeed, such descriptions and representations are the type of convenient labels used by those skilled in programming and/or the data processing arts to effectively convey the substance of their work to others skilled in the art. A person skilled in the art of programming may use these descriptions to readily generate specific instructions for implementing a program according to the present invention.

Often, for the sake of convenience only, it is preferred to implement and describe a program as various interconnected distinct software modules or features, individually and collectively also known as software. This is not necessary, however, and there may be cases where modules are equivalently aggregated into a single program with unclear boundaries. In any event, the software modules or features of this description may be implemented by themselves, or in combination with others. Even though it is said that the program may be stored in a computer-readable medium, it should be clear to a person skilled in the art that it need not be a single memory, or even a single machine. Various portions, modules or features of it may reside in separate memories, or even separate machines. The separate machines may be connected directly, or through a network, such as a local access network (LAN), or a global network, such as the Internet.

It will be appreciated that some of these methods may include software steps which may be performed by different modules of an overall software architecture. For example, data forwarding in a router may be performed in a data plane, which consults a local routing table. Collection of performance data may also be performed in a data plane. The performance data may be processed in a control plane, which accordingly may update the local routing table, in addition to neighboring ones. A person skilled in the art will discern which step is best performed in which plane.

An economy is achieved in the present document in that a single set of flowcharts is used to describe both programs, and also methods. So, while flowcharts are described in terms of boxes, they can mean both method and programs.

For this description, the methods may be implemented by machine operations. In other words, embodiments of programs are made such that they perform methods of the invention that are described in this document. These may be optionally performed in conjunction with one or more human operators performing some, but not all of them. As per the above, the users need not be collocated with each other, but each only with a machine that houses a portion of the program. Alternately, some of these machines may operate automatically, without users and/or independently from each other.

Methods are now described.

Figure 7:
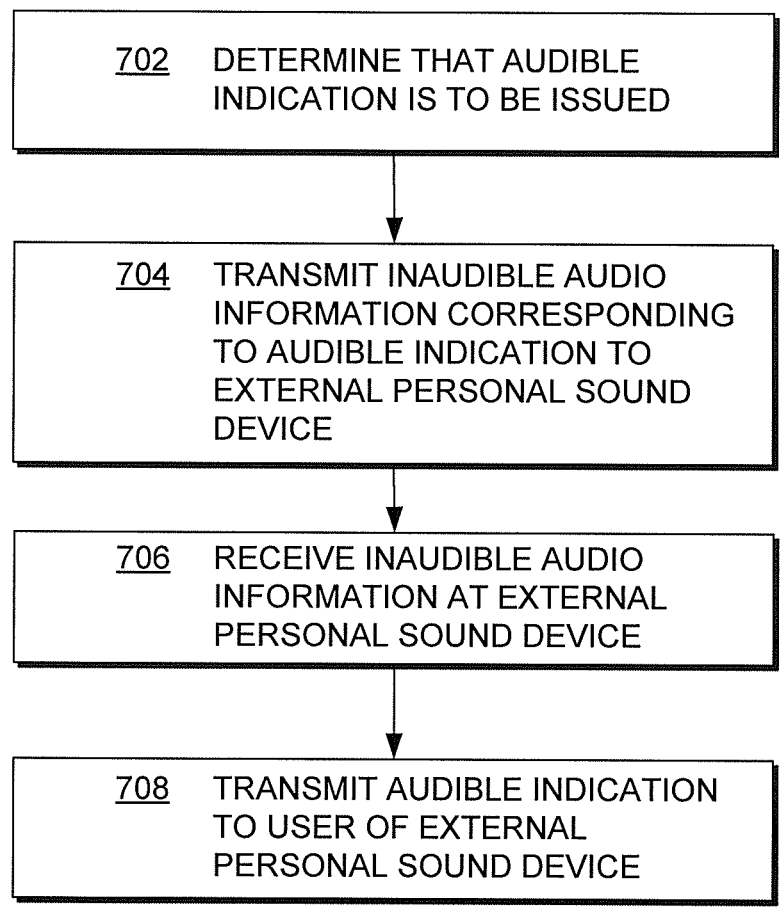
FIG. 7 is a flowchart for illustrating a method of delivering an audible indication to a user according to embodiments.

FIG. 7 is a flowchart for illustrating a method 700 of delivering an audible indication to a user according to embodiments. In an operation 702, a determination is made that an audible indication, such as a verbal prompt, is to be issued. This determination may be made by the audible indication control module 391 of FIG. 3, for example.

In an operation at 704, inaudible audio information corresponding to the audible indication to be issued is transmitted to an external personal sound device. The inaudible audio information may be transmitted by the communication module 490 of FIG. 4 to the first sound device 410 of FIG. 4, for example.

In an operation at 706, the sound device receives the inaudible audio information. In an operation at 708, the sound device transmits that audible indication to the user of the sound device. For example, the first sound device 410 of FIG. 4 may transmit the audible indication to the user 414 using the first sound device 410.

Figure 8:
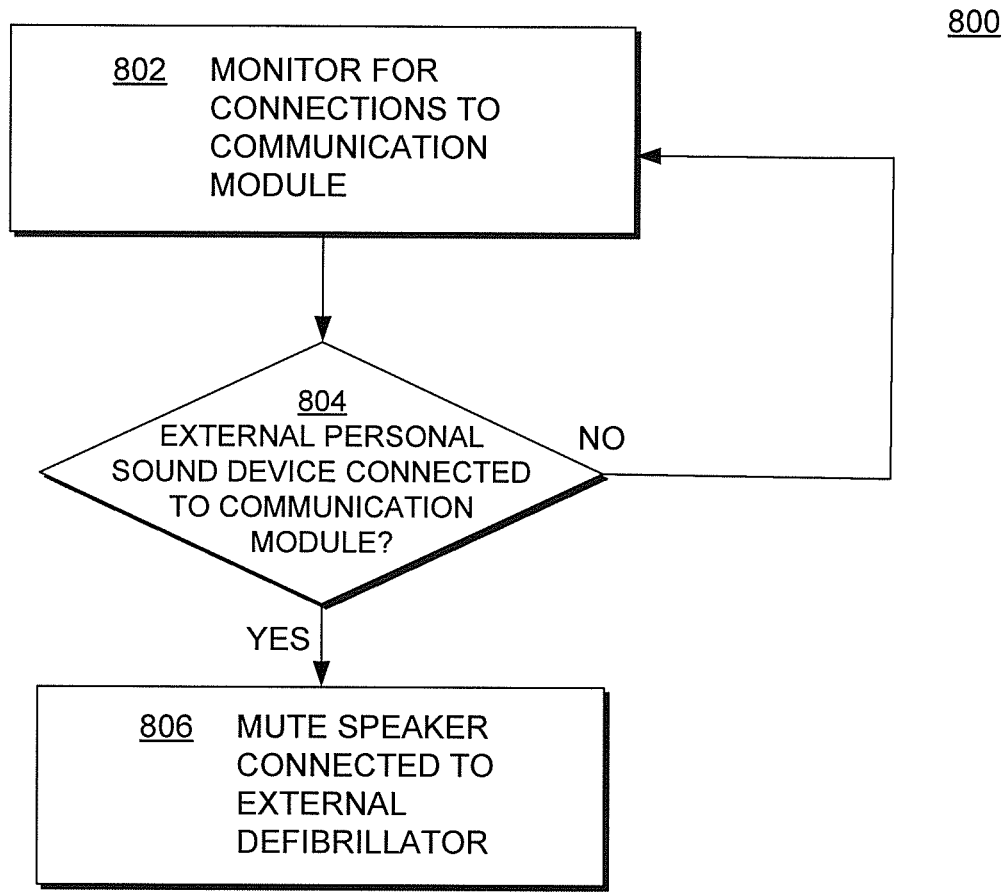
FIG. 8 is a flowchart for illustrating a method of muting a speaker responsive to an external personal device being connected to an external defibrillator according to embodiments.

FIG. 8 is a flowchart for illustrating a method 800 of muting a speaker responsive to an external personal device being connected to an external defibrillator according to embodiments. In an operation at 802, a defibrillator such as the defibrillator 400 of FIG. 4, for example, monitors for connections to a communication module, such as communication module 490 of FIG. 4, of the defibrillator.

In an operation at 804, a determination is made as to whether an external personal sound device, such as the sound devices 410, 420, and 431 of FIG. 4, is connected to the communication module. If so, the method 800 may proceed to an operation at 806, in which a speaker connected to the defibrillator is muted; otherwise, the method 800 may return to the operation at 802. Muting may be automatic, or conditional. If conditional, muting may be subject to a setting that has been made before the defibrillator is brought to the scene, or by a rescuer at the scene.

Figure 9:
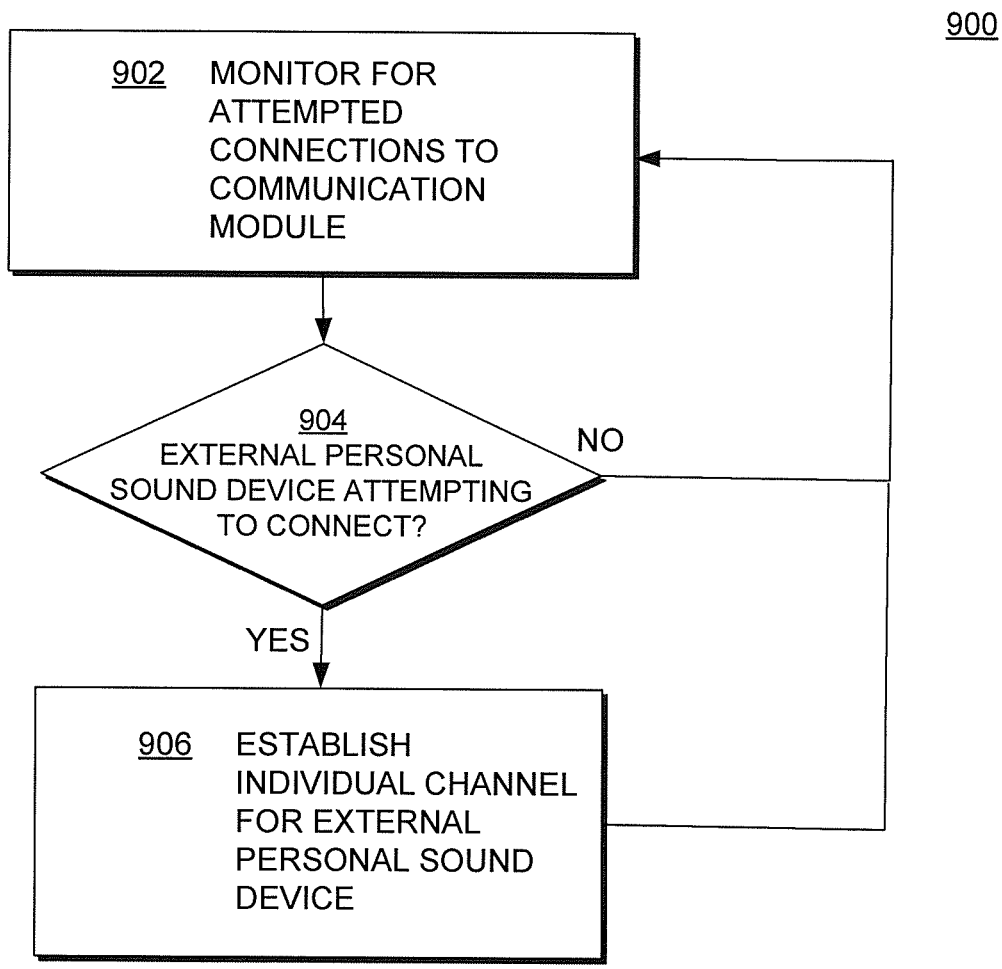
FIG. 9 is a flowchart for illustrating a method of establishing an individual channel for an external personal device responsive to the external personal device attempting to connect to an external defibrillator according to embodiments.

FIG. 9 is a flowchart for illustrating a method 900 of establishing an individual channel for an external personal device responsive to the external personal device attempting to connect to an external defibrillator according to embodiments. In an operation at 902, a defibrillator such as the defibrillator 400 of FIG. 4, for example, monitors for attempted connections to a communication module, such as communication module 490 of FIG. 4, of the defibrillator.

In an operation at 904, a determination is made as to whether an external personal sound device, such as the sound devices 410, 420, and 431 of FIG. 4, is attempting to connect to the communication module. If so, the method 900 may proceed to an operation at 906, in which an individual channel is established for the sound device attempting to connect to the communication module; otherwise, the method 900 may return to the operation at 902. The method 900 may also return to the operation at 902 after beginning or completing the operation at 906.

Figure 10:
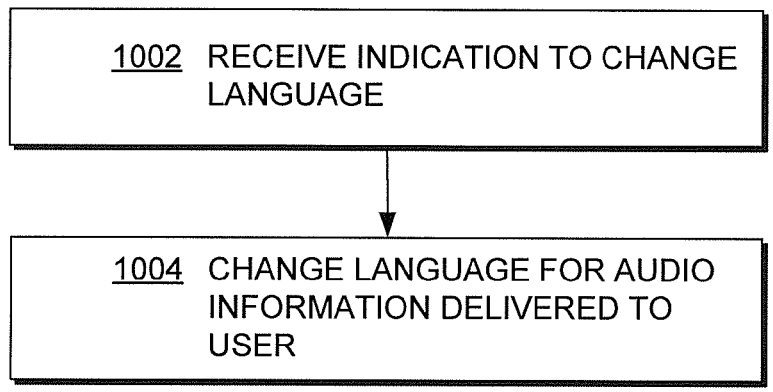
FIG. 10 is a flowchart for illustrating a method of changing a language for audio information delivered to a user according to embodiments.

FIG. 10 is a flowchart for illustrating a method 1000 of changing a language for audio information delivered to a user according to embodiments. In an operation at 1002, an indication to change language is received. For example, a user may use a control button, such as the control button(s) 395 of FIG. 3, or other interface means, to indicate that the audio information is to be delivered in a particular language to a user using an external personal sound device. Alternately, the language selection can be made via the socket that the sound device is connected to.

In an operation at 1004, the language for the audio information delivered to the user is changed responsive to the received indication to change language. For example, an external personal sound device may transmit an audible indication corresponding to the audio information in the language indicated by the received indication.

Figure 11:
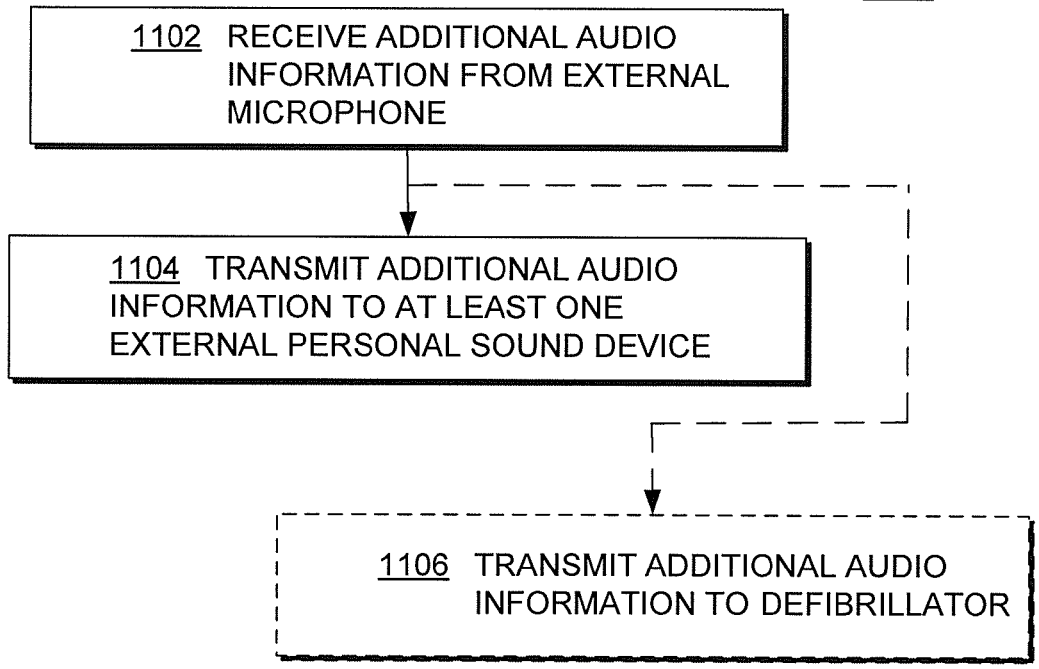
FIG. 11 is a flowchart for illustrating a method of transmitting additional audio information from an external microphone according to embodiments.

FIG. 11 is a flowchart for illustrating a method 1100 of transmitting additional audio information from an external microphone according to embodiments. In an operation at 1102, additional audio information is received by way of an external microphone, such as the external microphone 426 of FIG. 4, capturing a voice from a user using the external microphone, for example.

In an operation at 1104, the additional audio information may be transmitted to at least one external personal sound device. For example, the external microphone 426 of FIG. 4 may transmit a voice captured from the second user 424 to one or both of the first sound device 410 and third sound device 431. Moreover, the external input could be translated to another language for delivery to another sound device. The translation could be done in the defibrillator. The external microphone user could provide instruction in multiple languages, which would then be recognized and routed accordingly. The external input could be the selection of prerecorded prompts that would then be delivered in the appropriate language to the appropriate sound device.

In an optional operation at 1106, the additional audio information may be transmitted to a defibrillator. For example, the external microphone 426 of FIG. 4 may transmit the voice captured from the second user 424 to the communication module 490 of defibrillator 400. The defibrillator 400 may store the captured voice in connection with the patient's medical record, for example.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems.

The following claims define certain combinations and sub-combinations of elements, features, steps, and/or functions, which are regarded as novel and non-obvious. Additional claims for other combinations and sub-combinations may be presented in this or a related document.

What is claimed is:

1. A defibrillator for caring for a person, the defibrillator for use with a plurality of external personal sound devices each configured to receive inaudible audio information corresponding to an audible indication and deliver the audible indication to a user caring for the person responsive to receiving the inaudible audio information, the defibrillator comprising:

a housing that includes an energy storage module for storing an electrical charge;

a socket in the housing;

an other socket in the housing;

a defibrillation port for guiding via electrodes the stored electrical charge to the person;

a processor configured to determine whether the audible indication is to be issued to the user; and a communication module configured to, responsive to the processor determining that the audible indication is to be issued, transmit the inaudible audio information corresponding to the audible indication to the plurality of external personal sound devices, the transmitted inaudible audio information being inaudible to the user, wherein at least one of the plurality of external personal sound devices is configured to receive the inaudible audio information from the communication module through a wired connection, wherein the at least one of the plurality of external personal sound devices includes a plug configured to be received matingly in the socket, wherein the communication module is configured to transmit different inaudible audio information to the socket and to the other socket, and wherein the socket is an Advanced Life Support (ALS) socket and the other socket is a Basic Life Support (BLS) socket.

2. The defibrillator of claim 1, in which at least one of the plurality of external personal sound devices comprises an earpiece.

3. The defibrillator of claim 2, in which the earpiece is configured to be coupled with a helmet configured to be worn by the user.

4. The defibrillator of claim 2, in which the earpiece is configured to be coupled with a wearable display unit.

5. The defibrillator of claim 1, in which the communication module has a range of at least 300 feet.

6. The defibrillator of claim 1, in which at least one of the plurality of external personal sound devices is configured to receive the inaudible audio information from the communication module through a wireless connection.

7. The defibrillator of claim 6, in which the at least one of the plurality of external personal sound devices is located remotely from the defibrillator.

8. The defibrillator of claim 6, in which the wireless connection is a telephone connection.

9. The defibrillator of claim 1, in which at least one of the plurality of external personal sound devices is located remotely from the defibrillator.

10. The defibrillator of claim 1, further comprising:

at least one external microphone configured to:

capture a verbal input from an other user, and in which the communication module is further configured to transmit the captured verbal input as additional audio information to at least one of the plurality of external personal sound devices.

11. The defibrillator of claim 10, in which the communication module is configured to transmit the additional audio information to only the at least one of the plurality of external personal sound devices.

12. The defibrillator of claim 1, further comprising:

a memory storing prompt data that correspond to prompts in at least two different human languages, and in which prompt data that corresponds to one of the languages is transmitted as the inaudible audio information to at least one of the plurality of external personal sound devices according to a received language selection input.

13. The defibrillator of claim 12, in which
the prompt data corresponds to two different human languages, and
prompt data that corresponds to the other one of the languages is transmitted as the inaudible audio information to another one of the plurality of external personal sound devices according to an other received language selection input.

14. The defibrillator of claim 1, in which
at least one of the plurality of external personal sound devices is configured to:
deliver to the communication module a connection signal indicating that the at least one of the plurality of external personal sound devices is maintaining a connection to the communication module.

15. The defibrillator of claim 14, in which
the connection signal is selected from the group consisting of an audible signal, a visual signal, and a tactile signal.

16. The defibrillator of claim 14, in which
the connection signal is delivered via a user interface of the defibrillator.

17. The defibrillator of claim 14, in which
the connection signal is delivered to the at least one of the plurality of external personal sound devices as supplementary inaudible audio information.

18. The defibrillator of claim 1, further comprising:
a speaker configured to selectively deliver the audible indication to the user, and
in which the processor is further configured to:
monitor for connections to the communication module, and
responsive to the at least one of the plurality of external personal sound devices establishing a connection to the communication module, causing the audible indication to not be delivered via the speaker.

19. The defibrillator of claim 1, in which
the audible indication is selected from the group consisting of an alert pertaining to the defibrillator, a prompt directing a rescuer to perform a particular action with respect to the patient, and a characteristic sound indicating that a capacitor of the defibrillator is gradually being charged for delivering a shock.

20. The defibrillator of claim 1, in which
a channel is established between the communication module and each of the plurality of external personal sound devices.

* * * * *